US00PP34099P2

(12) United States Plant Patent
Barnes

(10) Patent No.: US PP34,099 P2
(45) Date of Patent: Apr. 5, 2022

(54) ***VERBENA* PLANT NAMED 'WNVESBIB'**

(50) Latin Name: *Verbena hybrida*
Varietal Denomination: WNVESBIB

(71) Applicant: Brent D. Barnes, Riverside, CA (US)

(72) Inventor: Brent D. Barnes, Riverside, CA (US)

(73) Assignee: WINGEN LLC, Mustang Ridge, TX (US)

( * ) Notice: Subject to any disclaimer, the term of this patent is extended or adjusted under 35 U.S.C. 154(b) by 0 days.

(21) Appl. No.: 17/371,559

(22) Filed: Jul. 9, 2021

(51) Int. Cl.
*A01H 6/86* (2018.01)
*A01H 5/02* (2018.01)

(52) U.S. Cl.
USPC ..... Plt./308

(58) Field of Classification Search
USPC ..... Plt./308
See application file for complete search history.

*Primary Examiner* — Annette H Para
(74) *Attorney, Agent, or Firm* — C. Anne Whealy

(57) ABSTRACT

A new and distinct cultivar of *Verbena* plant named 'WNVESBIB', characterized by its upright to outwardly spreading and mounding to trailing and decumbent plant habit; vigorous growth habit and rapid growth rate; freely branching habit; dark green-colored leaves; early and freely flowering habit; large inflorescences with large dark purple-colored flowers that are held above and beyond the foliar plane; and resistance to Powdery Mildew.

2 Drawing Sheets

Figure 1:
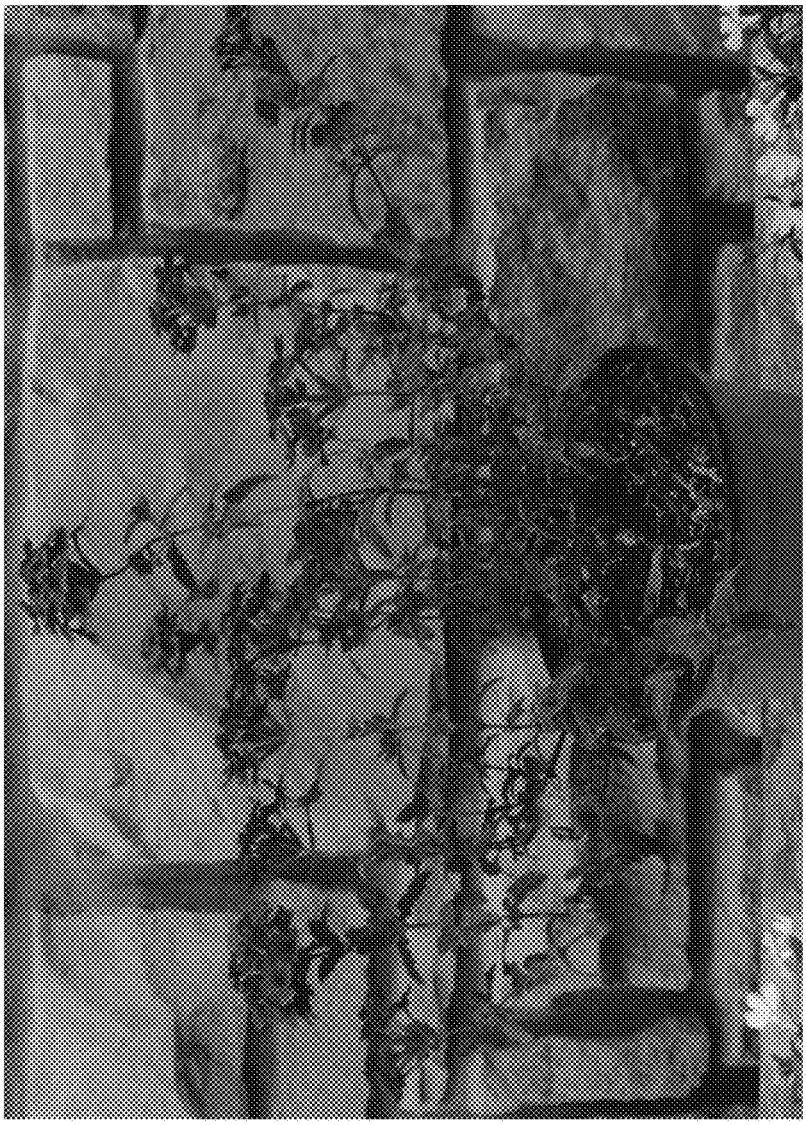

Botanical designation: *Verbena hybrida.*
Cultival Denomination: 'WNVESBIB'.

BACKGROUND OF THE INVENTION

The present invention relates to a new and distinct cultivar of *Verbena* plant, botanically known as *Verbena hybrida* and hereinafter referred to by the name 'WNVESBIB'.

The new *Verbena* plant is a product of a planned breeding program conducted by the Inventor in Bonsall, Calif. The objective of the breeding program is to create new vigorous and freely-branching *Verbena* plants with numerous large flowers and good garden performance.

The new *Verbena* plant originated from a cross-pollination made by the Inventor on Aug. 31, 2017 in Bonsall, Calif. of a proprietary seedling selection of *Verbena hybrida* identified as code number 17V508-01, not patented, as the female, or seed, parent with *Verbena hybrida* 'RIKAV18302', disclosed in U.S. Plant Pat. No. 25,396, as the male, or pollen, parent. The new *Verbena* plant was discovered and selected by the Inventor as a single flowering plant from within the progeny of the stated cross-pollination in a controlled greenhouse environment in Bonsall, Calif. on Aug. 2, 2018.

Asexual reproduction of the new *Verbena* plant by vegetative terminal cuttings in a controlled environment in Bonsall, Calif. since Aug. 6, 2018, has shown that the unique features of this new *Verbena* plant are stable and reproduced true to type in successive generations.

SUMMARY OF THE INVENTION

Plants of the new *Verbena* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'WNVESBIB'. These characteristics in combination distinguish 'WNVESBIB' as a new and distinct *Verbena* plant:

1. Upright to outwardly spreading and mounding to trailing and decumbent plant habit.
2. Vigorous growth habit and rapid growth rate.
3. Freely branching habit.
4. Dark green-colored leaves.
5. Freely flowering habit.
6. Large inflorescences with large dark purple-colored flowers that are held above and beyond the foliar plane.
7. Resistance to Powdery Mildew (*Podosphaera xanthii*).

Plants of the new *Verbena* can be compared to plants of the female parent selection. Plants of the new *Verbena* differ primarily from plants of the female parent selection in the following characteristics:

1. Plants of the new *Verbena* are more spreading than and not as upright as plants of the female parent selection.
2. Plants of the new *Verbena* have larger inflorescences and larger flowers than plants of the female parent selection.
3. Plants of the new *Verbena* have darker purple-colored flowers than plants of the female parent selection.
4. Flowers of plants of the new *Verbena* do not fade as much as flowers of plants of the female parent selection.

Plants of the new *Verbena* can be compared to plants of the male parent, 'RIKAV18302'. Plants of the new *Verbena* differ primarily from plants of 'RIKAV18302' in the following characteristics:

1. Plants of the new *Verbena* have larger inflorescences and larger flowers than plants of 'RIKAV18302'.
2. Plants of the new *Verbena* have dark purple-colored flowers whereas plants of 'RIKAV18302' have lighter-colored flowers with white-colored centers.

Plants of the new *Verbena* can be compared to plants of the *Verbena hybrida* 'AKIV571-1', disclosed in U.S. Plant Pat. No. 23,051. In side-by-side comparisons, plants of the new *Verbena* differ primarily from plants of 'AKIV571-1' in the following characteristics:

1. Plants of the new *Verbena* are more vigorous than plants of 'AKIV571-1'.
2. Plants of the new *Verbena* are more mounding than and not as prostrate as plants of 'AKIV571-1'.
3. Plants of the new *Verbena* have larger flowers than plants of 'AKIV571-1'.
4. Plants of the new *Verbena* have dark purple-colored flowers whereas plants of 'AKIV571-1' have violet-colored flowers.

Plants of the new *Verbena* can also be compared to plants of the *Verbena hybrida* 'Vepita Blue-Violet', not patented. In side-by-side comparisons, plants of the new *Verbena* differ primarily from plants of 'Vepita Blue-Violet' in the following characteristics:

1. Plants of the new *Verbena* are more vigorous than and not as compact as plants of 'Vepita Blue-Violet'.
2. Plants of the new *Verbena* are more mounding than and not as prostrate as plants of 'Vepita Blue-Violet'.
3. Plants of the new *Verbena* have larger leaves than plants of 'Vepita Blue-Violet'.
4. Plants of the new *Verbena* have larger flowers than plants of 'Vepita Blue-Violet'.
5. Plants of the new *Verbena* are resistant to Powdery Mildew whereas plants of 'Vepita Blue-Violet' are susceptible to Powdery Mildew.

BRIEF DESCRIPTION OF THE PHOTOGRAPHS

The accompanying colored photographs illustrate the overall appearance of the new *Verbena* plant showing the colors as true as it is reasonably possible to obtain in colored reproductions of this type. Colors in the photographs may differ slightly from the color values cited in the detailed botanical description which accurately describe the colors of the new *Verbena* plant.

The photograph on the first sheet (FIG. 1) is a side perspective view of a typical flowering plant of 'WNVESBIB' grown in a container.

Figure 2:
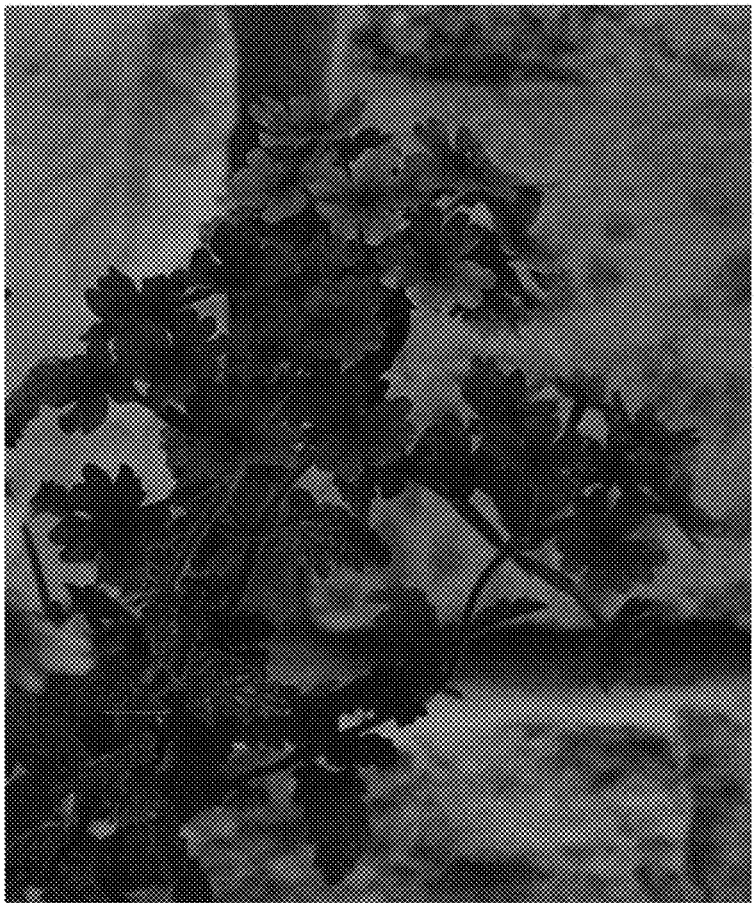

The photograph on the second sheet (FIG. 2) is a close-up view of a typical flowering plant of 'WNVESBIB'.

DETAILED BOTANICAL DESCRIPTION

The aforementioned photographs and following observations and measurements describe plants grown during the late summer and early autumn in 15.24-cm containers in a corrugated polycarbonate-covered greenhouse in Carlton, Mich. and under cultural practices typical of commercial *Verbena* production. During the production of the plants, day temperatures averaged 26° C., night temperatures averaged 20° C. and light levels averaged 9,290 foot-candles. Plants were pinched three weeks after planting and were twelve weeks from planting rooted cuttings when the photographs and description were taken. In the following description, color references are made to The Royal Horticultural Society Colour Chart, 2015 Edition, except where general terms of ordinary dictionary significance are used.

Botanical classification: *Verbena hybrida* 'WNVESBIB'.

Parentage:

*Female, or seed, parent.*—Proprietary seedling selection of *Verbena hybrida* identified as code number 17V508-01, not patented.

*Male, or pollen, parent.*—*Verbena hybrida* 'RIKAV18302', disclosed in U.S. Plant Pat. No. 25,396.

Propagation:

*Type cutting.*—Vegetative terminal cuttings.

*Time to initiate roots, summer.*—About three to four days at temperatures ranging from about 17° C. to 29° C.

*Time to initiate roots, winter.*—About five to seven days at temperatures ranging from about 17° C. to 21° C.

*Time to produce a rooted plant, summer.*—About three weeks at temperatures ranging from about 17° C. to 29° C.

*Time to produce a rooted plant, winter.*—About four weeks at temperatures ranging from about 17° C. to 21° C.

*Root description.*—Fine, fibrous; typically white in color, actual color of the roots is dependent on substrate composition, water quality, fertilizer type and formulation, substrate temperature and physiological age of roots.

*Rooting habit.*—Freely branching; medium density.

Plant description:

*Plant and growth habit.*—Upright to outwardly spreading and mounding to trailing and decumbent plant habit; freely branching habit with lateral branches potentially developing at every node, pinching enhances branching potential; dense and bushy plant habit; vigorous growth habit and rapid growth rate.

*Plant height.*—About 31 cm.

*Plant diameter* (*spread*).—About 57 cm.

Lateral branch description:

*Length.*—About 26 cm.

*Diameter.*—About 3.5 mm to 4 mm.

*Internode length.*—About 3 cm.

*Orientation.*—Initially upright then outwardly spreading to trailing and decumbent.

*Strength.*—Strong; flexible.

*Texture and luster.*—Moderately pubescent; slightly glossy; becoming woody with subsequent development.

*Color, developing.*—Close to 144A.

*Color, developed.*—Close to 144A; if woody, close to 199A.

Leaf description:

*Arrangement.*—Opposite, simple.

*Length.*—About 5 cm to 5.75 cm.

*Width.*—About 2.5 cm to 3.2 cm.

*Shape.*—Deltoid, elongated.

*Apex.*—Acute.

*Base.*—Truncate.

*Margin.*—Dentate to serrate.

*Texture and luster, upper surface.*—Sparsely to moderately pubescent, rough; glossy.

*Texture and luster, lower surface.*—Mostly glabrous with pubescence along veins and margins; slightly glossy.

*Venation pattern.*—Pinnate.

*Color.*—Developing leaves, upper surface: Darker green than 146A. Developing leaves, lower surface: Close to 146A to 146B. Fully expanded leaves, upper surface: Close to 147A; venation, close to 146A. Fully expanded leaves, lower surface: Close to 147B; venation, close to 146A to 146B.

*Petioles.*—Length: About 1 cm. Diameter: About 2.5 mm. Strength: Strong; flexible. Texture and luster, upper and lower surfaces: Pubescent; slightly glossy. Color, upper surface: Close to 144B. Color, lower surface: Close to 146B.

Flower description:

*Flower arrangement and habit.*—Sessile salverform flowers arranged in upright hemispherical terminal corymbs; flowers face upward or outwardly depending on the position in the inflorescence; freely flowering habit with about 24 flowers developing per inflorescence with numerous inflorescences developing per plant during the flowering season.

*Natural flowering season.*—Plants flower continuously from spring until the autumn; early flowering habit, plants begin flowering about five to six weeks after planting.

*Flower longevity.*—Flowers last about five days on the plant; flowers not persistent.

*Fragrance.*—None detected.

*Inflorescence height.*—About 3.5 cm.

*Inflorescence diameter.*—About 5.5 cm.

*Flower buds.*—Length: About 1 cm. Diameter: About 7.5 mm. Shape: Elongated oblong. Texture and luster: Pubescent; moderately glossy. Color: Close to 146A.

*Flower diameter.*—About 2.25 cm.

*Flower depth (height).*—About 3 cm.

*Throat diameter.*—About 2 mm.

*Tube length.*—About 2.7 cm.

*Tube diameter, proximally.*—About 1.5 mm.

*Corolla.*—Arrangement: Single whorl of five fused petals fused towards the base into a slender narrow tube. Petal lobe length: About 1 cm. Petal lobe width: About 9 mm. Petal lobe shape: Roughly cordate. Petal lobe apex: Retuse. Petal margin: Entire; slightly undulate. Petal texture and luster, upper surface: Smooth, glabrous; velvety; matte. Petal texture and luster, lower surface: Smooth, glabrous; matte. Throat texture and luster: Moderately pubescent; matte. Tube texture and luster: Moderately pubescent; matte. Color: Petal lobes, when opening and fully opened, upper surface: Close to 79A; venation, close to 79A; color becoming closer to 79D with subsequent development. Petal lobes, when opening and fully opened, lower surface: Close to 79A to 79B; venation, close to 79A to 79B; color becoming closer to 79D with subsequent development. Throat: Close to 79A to 79B; venation, close to 79A to 79B. Tube: Close to 145D variably tinged with close to 79A to 79B; venation, similar to lamina colors.

*Calyx.*—Arrangement: Single whorl of five fused sepals fused towards the base into a slender tube. Length: About 1.4 cm. Diameter: About 3 mm. Sepal length: About 1.4 cm. Sepal width: Less than 1 mm. Sepal shape: Acicular. Sepal apex: Acuminate. Sepal margin: Entire. Sepal texture and luster, upper surface: Pubescent; slightly glossy. Sepal texture and luster, lower surface: Pubescent; moderately glossy. Sepal color, upper and lower surfaces: Close to 144A.

*Peduncles.*—Length: About 4 cm to 4.5 cm. Diameter: About 2 mm. Strength: Strong; flexible, wiry. Aspect: Mostly upright. Texture and luster: Pubescent; slightly glossy. Color: Close to 144A.

*Reproductive organs.*—Stamens: Quantity and arrangement: Five per flower, filaments partially adnate to corolla tube. Filament length: About 1 cm. Filament color: Close to 145D. Anther size: About 0.75 mm by 1 mm. Anther shape: Oblong. Anther color: Close to 151D. Pollen amount: None observed. Pistils: Quantity: One per flower. Pistil length: About 1.75 cm. Stigma shape: Bi-parted. Stigma diameter: About 1 mm by 1.5 mm. Stigma color: Close to 144A. Style length: About 1.5 cm. Style color: Close to 145D. Ovary color: Close to 144A. Fruits and seeds: To date, fruit and seed development have not been observed on plants of the new *Verbena*.

Temperature tolerance: Plants of the new *Verbena* have been observed to tolerate temperatures from about 2° C. to about 40° C. and are suitable for USDA Hardiness Zones 8a to 11 b.

Pathogen & pest resistance: Plants of the new *Verbena* have been observed to be resistant to Powdery Mildew (*Podosphaera xanthii*). To date, plants of the new *Verbena* have not been observed to be resistant to pests and other pathogens common to *Verbena* plants.

It is claimed:

1. A new and distinct *Verbena* plant named 'WNVESBIB' as illustrated and described.

* * * * *